United States Patent [19]

Johnson, III

[11] 4,320,657

[45] Mar. 23, 1982

[54] PARTICULATE FLOWMETER

[75] Inventor: Joseph L. Johnson, III, Hockessin, Del.

[73] Assignee: ICI Americas Inc., Wilmington, Del.

[21] Appl. No.: 144,917

[22] Filed: Apr. 29, 1980

[51] Int. Cl.³ ............................................. G01F 15/00
[52] U.S. Cl. .................................................. 73/432 R
[58] Field of Search ...................................... 73/432 R

[56] References Cited

U.S. PATENT DOCUMENTS

| | | | |
|---|---|---|---|
| 2,633,027 | 3/1953 | Bunnell | 73/432 |
| 3,221,560 | 12/1965 | Kosa et al. | 73/432 |
| 3,345,880 | 10/1967 | Boenisch | 73/432 |
| 3,376,753 | 4/1968 | Pitkin et al. | 73/432 |
| 3,665,768 | 5/1972 | Hosokawa et al. | 73/432 |

OTHER PUBLICATIONS

Danish F. Q. and Parrot E. L.; J. Pharm. Sci.; 60; p. 548; 1971, "Flow Rates of Solid Particulate Pharmaceuticals".
Harwood, C. F. and Pilpel N.; J. Pharm. and Pcol.; 21; p. 721; 1969, "The Flow of Granular Solids Through Circular Orifices".
Gold, Duvall, and Palermo; J. Pharm. Sci.; 55, p. 1133; 1966, "Powder Flow Studies 1".
Gold, Duvall, Palermo and Slater; J. Pharm. Sci.; 55, p. 1291; 1966, "Powder Flow Studies 2".

Primary Examiner—Donald O. Woodiel

[57] ABSTRACT

An apparatus for measuring the flowability of particulate materials from a vessel through a die metering means.

6 Claims, 5 Drawing Figures

PARTICULATE FLOWMETER

This invention relates to an apparatus and method for measuring the relative flowability of particulate materials.

More particularly, the present apparatus is for use in a laboratory, or similar setting, for the purpose of studying the flow rate of powdered or granular materials in a reproducible manner in such a way that the results can be correlated with actual operating conditions in commercial tablet making machines.

Prior to the present invention, there didn't appear to be any commercially available flow-measuring apparatus or flowmeter which duplicated the many orifice configurations encountered in commercial tablet making machines and the manner or conditions under which powdered or granular materials are presented to this type orifice in such machines.

The apparatus and method of the present invention can be used in any field wherein dies are filled with powdered or granular materials and compacted, e.g., pharmaceuticals, foods, confectionary, metals, ceramic and other non-metal compacts.

There are several different known designs for flow-meters. In general all of these use some type of retaining vessel to hold the sample of particulate material the flow of which is to be measured through an orifice. Examples of such apparatus is disclosed in U.S. Pat. No. 3,376,753 and No. 3,221,560. However, this prior art apparatus does not appear to provide for the use of the exact dies which are used in commercial tablet making machines as the orifice in the flow-measuring apparatus and experiments indicate that the shape of the die affects the flowability of the powdered or granular materials being tested. Thus interchangeability of dies which duplicate the situations encountered in actual practice is important in flow measurement.

It is an object of the present invention to provide a flow-measuring apparatus and method for determining the relative flowability of powdered or granular materials.

Another object of the present invention is to provide a laboratory instrument for rheological study of particulate materials, the results of which can be related to commercial tablet making equipment.

A further object of the present invention is to provide a method to obtain flowability indices for predicting the flowability of particulate materials in a commercial tablet making machine.

These and other objects of the subject invention are obtained by an apparatus for determining the flowability of powdered or granular material comprising (a) a vertically disposed vessel having an upper orifice and a lower orifice, (b) said lower orifice surrounded by a bottom portion of said vessel which bottom portion has an inner face and an outer face, (c) a metering means, having an opening therethrough, positioned against the said outer face so that the opening in the metering means is in unobstructed communication with the lower orifice, and (d) a moveable retaining means mounted on said vessel to hold said metering means in tight contact with the said outer face.

The objects of the present invention, will be apparent from the following description of the present invention taken in connection with the following drawings.

Figure 1:
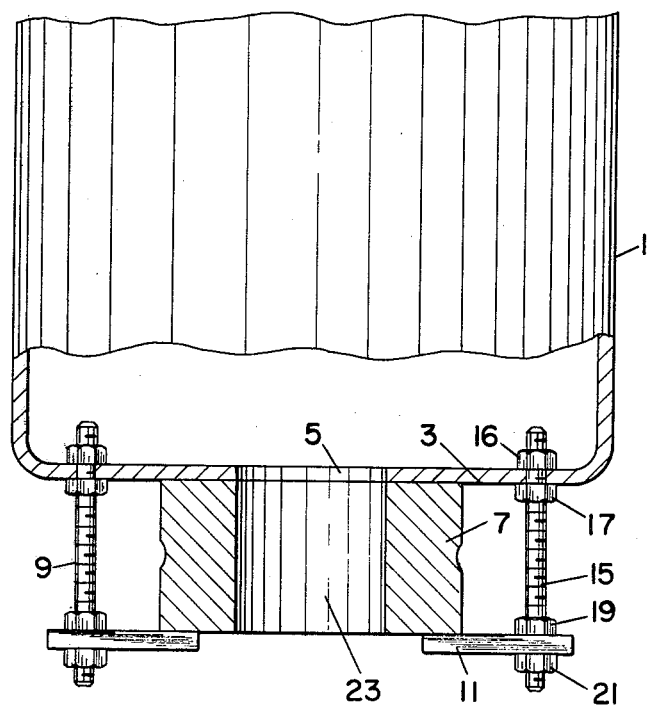
FIG. 1 is an elevational and partially cross-sectional view of an embodiment of the present apparatus.

Referring to the drawings in which like numerals are employed to designate like parts throughout, the basic elements of the present apparatus are shown in FIG. 1 wherein 1 is a vessel having a bottom portion 3 and a lower orifice or opening 5. Lower orifice 5 is preferably round in shape, but can suitably be any shape. Placed beneath bottom portion 3 is pharmaceutical tablet die 7. Die 7 is held in tight contact with bottom 3 by retaining means designated generally 9 which is adjustable in order to accomodate a range of sizes of die 7. Vessel 1 can be any suitable shape but in most instances will be cylindrical, cone or funnel in shape.

Figure 2:
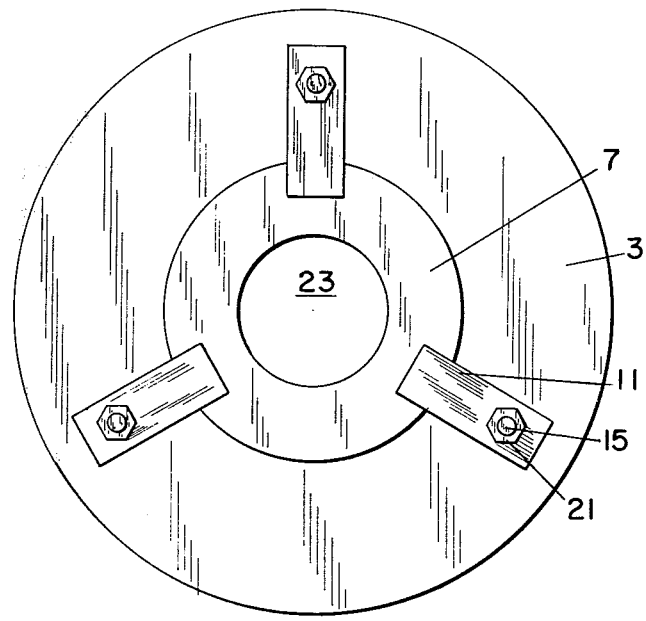
FIG. 2 is a bottom view of the apparatus of FIG. 1.
Figure 3:
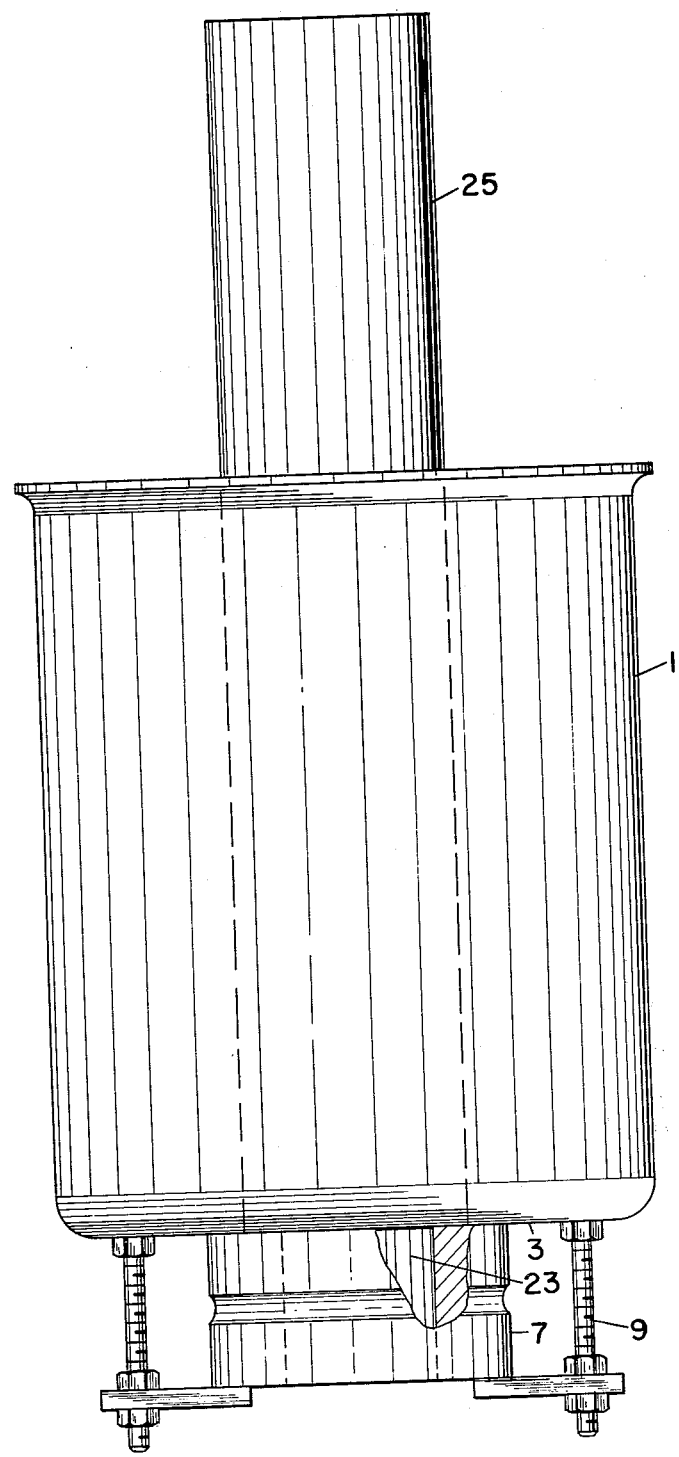
FIG. 3 is an elevational and partially cross-sectional view of another embodiment of the present invention.

In FIGS. 1, 2 and 3, die 7 is held tightly against bottom 3 by bracket means 11 which is anchored to bottom 3 through bolt 15. Bolt means 15 is anchored through and to bottom 3 by nuts 16 and 17 as shown in cross-section in FIG. 1. Bracket means 11 is fastened on to bolt means 15 by nuts 19 and 21. In FIGS. 1 and 2 opening 23 extends through the center of die 7 in communication with opening 5 in bottom 3. Opening 23 in die 7 can be of any desired shape or size used to make commercially useable tablets. For example, die 7 can have a suitable opening 23 to make a round, capsule, square or star shaped tablet.

Lower orifice 5 is the same diameter or greater in diameter than the diameter of opening 23 in die 7 but less in diameter than the outside diameter of die 7 so that the entirety of opening 23, no matter what its shape, is in unobstructed communication with lower orifice 5 of vessel 1. Obviously, the outer diameter of die 7 must be greater in diameter than the diameter of orifice 5 so that it can be held tight against bottom portion 3 of vessel 1 and not be pushed through orifice 5 when placed in operating position. If lower orifice 5 and opening 23 in die 7 are other than round in shape, the same relationship of opening sizes must be maintained so as to provide for the unobstructed flow of particulate material through orifice 5 of vessel 1 into and through opening 23 in die 7.

In FIG. 3, hollow column or tube 25 is positioned centrally in vessel 1 so as to make contact with the inner surface of bottom 3. The inner diameter of column 25 must be of a greater diameter than the diameter of opening 23 in die 7. Therefore, suitably the inner diameter of column 25 will range from 1" to 2". Column 25 can be suitably positioned in vessel 1 and held in place with a standard chemical laboratory clamp and ring stand if needed, when the supply of powdered or granular material to be tested is not sufficient in volume to fill vessel 1 to the desired level. Obviously, hollow column 25 can be filled with much less material than is necessary to fill vessel 1.

Figure 4:
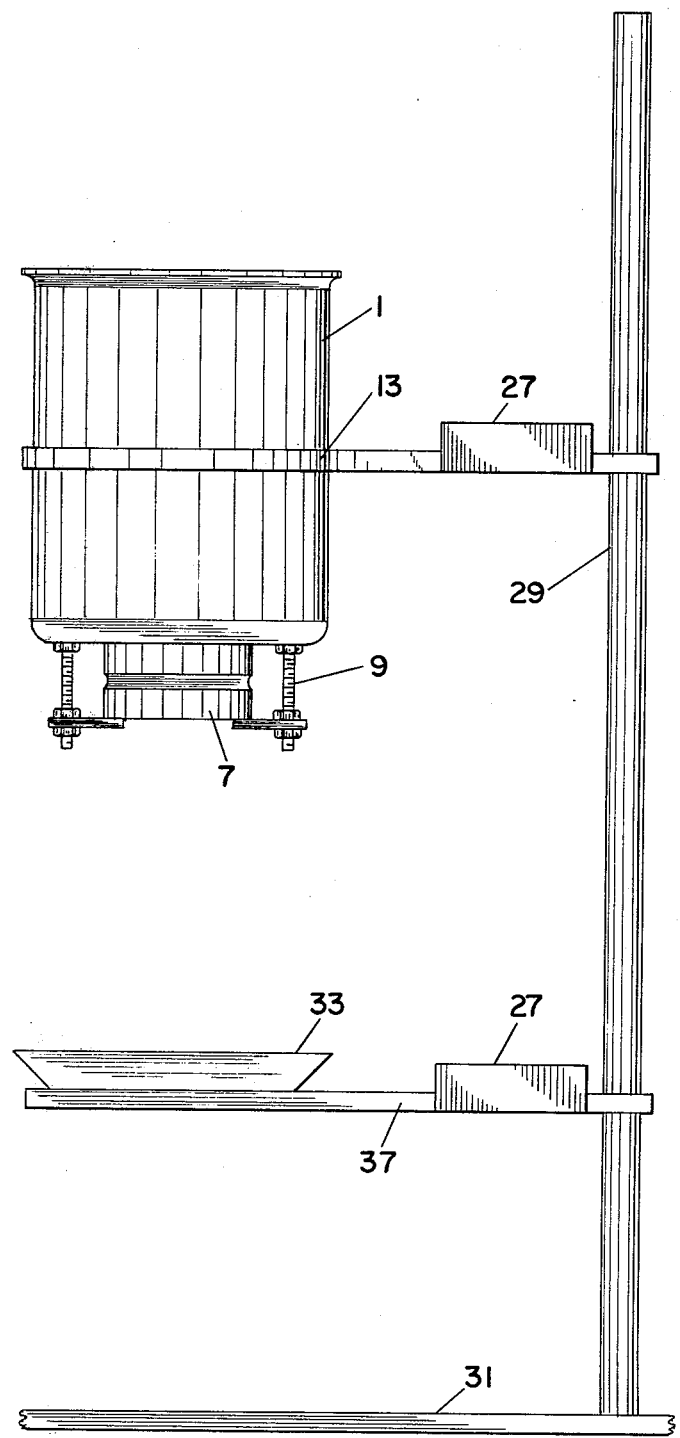
FIG. 4 is a schematic view of an apparatus of the present invention.

Schematic FIG. 4 shows vessel 1 having die 7 functionally attached thereto by retaining means 9. The unitary structure of vessel 1 and die means 7 is attached by a bracket or clamping means 13 through a strain gage beam balance 27 to a vertical support 29 which in turn is securely anchored to table top 31. Beneath vessel 1 and attached to vertical support 29 is a collecting plate 33 which is anchored to upright 29 through another strain gage beam balance 27.

Figure 5:
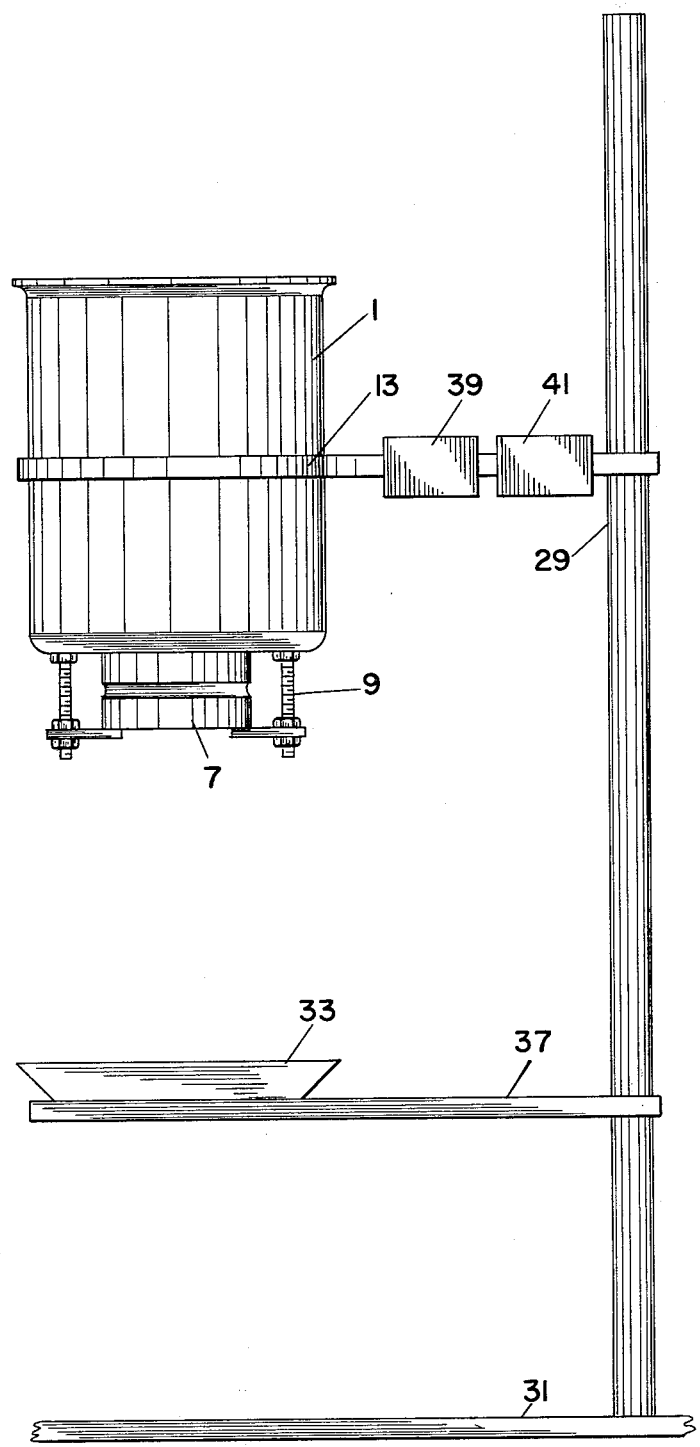
FIG. 5 is a schematic view of another embodiment of the present invention.

FIG. 5 shows the same apparatus as that shown in FIG. 4 except the flowmeter apparatus of the present invention is attached to vertical support 29 through a vibrator 39 and accelerometer 41.

In using one embodiment of the present apparatus, a plugging means or a flow restrictor (which can be a mechanical valve, shutter means, flat plate or even a human finger) is operatively placed over the bottom side or lower end of opening 23 on the bottom side of die 7 so as to stop any flow of the powdered or granular material to be tested. The valve, shutter means or flat plate can suitably be made from the same material as die 7. Then a quantity of granular or powdered material to be evaluated for flowability is poured into vessel 1 which also results in the filling of opening 23 in die 7 with the said granular or powdered material. At the desired time, a timing means, such as a stopwatch, is started and at the same instant the plugging means or flow restrictor is opened or removed from opening 23 in die 7. The time for the given quantity of powdered or granular material to pass from vessel 1 and through die 7 is recorded.

In another embodiment through the use of strain gage beam balance 27, instantaneous variation in the flow rate of particulate material through the subject flowmeter (as shown in FIG. 1) can be measured. Strain gauge beam balance 27 can be operationally connected with collection plate 33, as shown in FIG. 4, to produce through support means 37 an analog signal wherein voltage output increases with mass of particulate material gained in collection plate 33. If this voltage output over time is copied by a strip chart recorder, (available from Linseis Inc., Princeton Jct., N.J. 088500) a visual flow curve will result. This curve will not be a straight line but will reflect the internal variations in flow which are not accounted for by the simple mass per unit time measurement which averages out these variations. In this way the smoothness of the flow itself can be compared between two different powder blends as well as the mass per unit time.

Similarly, as illustrated in FIG. 4, a strain gage beam balance 27 can also be placed in operational relationship with clamping means or bracket 13 so that it can be used in exactly the same fashion as described above. Further this strain gage beam balance 27 can also be connected to a strip chart recorder. With such an apparatus the rate of powder or particulate material loss is determined and a flow curve is obtained which is the approximate inverse of the accumulative flow curve. However, the differential between these two curves will allow the determination of the quantity of powder in free fall between vessel 1 and collection plate 33.

In FIG. 5 vibrator 39 and an accelerometer 41 are operationally connected to clamping means 13. Accelerometer 41 quantifies the amount of vibration applied. In some instances when particulate solids undergo flow as in a pharmaceutical tabletting machine, vibrations occur during the operation of the machine. Increased vibrations tend to accelerate powder flow. Therefore, if the amount of tablet machine vibration can be quantified, then a like quantity of vibration can be applied to the unitary structure of vessel 1 and die 7 as shown in FIG. 5 in such a fashion as to duplicate the actual conditions under which the powder will flow. By using this method, the accuracy of powder flow measurement with respect to actual operating conditions is increased. Obviously, though not shown in FIG. 5, a strain gage beam balance 27 could also be placed in operational connection with support means 37 as shown in FIG. 4 and utilized as described above in relation to FIG. 4.

In a preferred embodiment of the present invention pharmaceutical die 7 for human use has an outside diameter of one to two inches, whereas die 7 for veterinary use has an outside diameter of two to four inches. The height of such dies whether for human or veterinary are within the range of three-fourths to two inches. The dimensions of opening 23 in die 7 are suitably dependent upon the size and shape tablet disired. For example, if a round tablet is desired, opening 23 may range from about one-eighth inch to one inch in diameter. Vessel 1 can suitably be of any convenient size for laboratory testing but generally is within the range of 300 ml. to 1,000 ml. However, it has been found that in may incidents, it is preferred to use a vessel having a capacity of about 500 ml. Vessel 1 in the preferred embodiment is cylindrical in shape. Bottom 3 of vessel 1 has a thickness of from about 0.020 inches to 0.030 inches but more preferably a thickness of about 0.025 inches to 0.030 inches. The side walls of vessel 1 can be of the same thickness as bottom 3 or thicker if desired.

All parts of the present apparatus can be prepared from or made from any suitable material. For example, vessel 1 can be made of plastic, metallic, or glass. Any suitable plastic can be used such as, polystyrene, polyvinylchloride or polypropylene. Suitable metallic materials include stainless steel, brass and copper. Die 7 can be made of any of the same plastic or metallic materials which are suitable for preparation of vessel 1. Retaining means 9 can be suitably made from metal or plastic of the type indicated above. Hollow column 25 can be made of the same materials as vessel 1. Clamping means 13 and support means 37 along with vertical support 29 are suitably made of any metal, such as steel, and are commercially available.

A strain gage beam balance, suitable for use in the present assembly, is commercially available from Micro Measurements Co., Romulus, Mich. 48174 under the model designation No. 125TF. A vibration 39 suitable for use in the present assembly is commercially available from Curtin Matheson Scientific Co., Wayne, N.J. 07470 under the model designation No. 55-180. An accelerometer 41 suitable for assembly with vibrator 39 to make a suitable vibrator-accelerometer assembly is available from Measurements Inc., P.O. Box 948, Frazer, Pa. 19355 under the designation Entran Miniature Accelerometer.

What is claimed is:

1. An apparatus for determining the flowability of powdered or granular material which comprises (a) a vertically disposed vessel having an upper orifice and a lower orifice, (b) said lower orifice surrounded by a bottom portion of said vessel which bottom portion has an inner face and an outer face, (c) a pharmaceutical tablet die, having an opening therethrough, positioned against the outer face so that the opening in the die is in unobstructive communications with the lower orifice, (d) a hollow column centrally positioned in said vessel so that the lower end of said column is positioned against the inside face of said vessel, and (e) a moveable retaining means mounted on said vessel to hold said die in tight contact with the said outer face.

2. An apparatus of claim 1 wherein the vessel is substantially cylindrical in shape.

3. An apparatus of claim 1 containing means for imparting a controlled vibration of said vessel and connected die.

4. An apparatus of claim 1 wherein the shape opening in the said pharmaceutical die is selected from the group consisting of oval, square, star, round, capsule and polygon.

5. An apparatus of claim 1 having in conjunction therewith means for measuring the output rate of the material passing through said die.

6. An apparatus for determining the flowability of powdered or granular material which comprises (a) a vertically disposed vessel having an upper orifice and a lower orifice, (b) said lower orifice surrounded by a bottom portion of said vessel which bottom portion has an inner face and an outer face, (c) a pharmaceutical tablet die, having an opening therethrough, positioned against the outer face so that the opening in the die is in unobstructive communication with the lower orifice, and (d) a moveable retaining means mounted on said vessel to hold said die in tight contact with the said outer face.

* * * * *